US00PP32694P3

(12) United States Plant Patent
Barnes

(10) Patent No.: US PP32,694 P3
(45) Date of Patent: Dec. 22, 2020

(54) ***SALVIA* PLANT NAMED 'BBSAL01301'**

(50) Latin Name: *Salvia hybrida*
Varietal Denomination: BBSAL01301

(71) Applicant: Brent D. Barnes, Riverside, CA (US)

(72) Inventor: Brent D. Barnes, Riverside, CA (US)

(73) Assignee: PLANT 21 LLC, Bonsall, CA (US)

( * ) Notice: Subject to any disclaimer, the term of this patent is extended or adjusted under 35 U.S.C. 154(b) by 0 days.

(21) Appl. No.: 16/873,534

(22) Filed: Apr. 30, 2020

(65) Prior Publication Data

US 2020/0367417 P1 Nov. 19, 2020

(30) Foreign Application Priority Data

May 17, 2019 (CA) ..... PBR 19-9879

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
See application file for complete search history.

*Primary Examiner* — Annette H Para
(74) *Attorney, Agent, or Firm* — C. A. Whealy

(57) ABSTRACT

A new and distinct cultivar of *Salvia* plant named 'BBSAL013201', characterized by its upright plant habit; moderately vigorous growth habit and rapid growth rate; freely branching habit; dense and bushy plant form; strong and sturdy lateral branches; dark green-colored leaves; early and freely flowering habit; upright inflorescences with purplish blue-colored flowers; and good garden performance.

1 Drawing Sheet

Botanical designation: *Salvia hybrida.*
Cultivar denomination: 'BBSAL013201'.

CROSS-REFERENCE TO A RELATED APPLICATION AND STATEMENT REGARDING PRIOR DISCLOSURES BY INVENTOR/APPLICANT

This application claims priority to a Canadian Plant Breeders' Rights application filed on May 17, 2019, application number 19-9879. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Salvia* plant, botanically known as *Salvia hybrida* and hereinafter referred to by the name 'BBSAL013201'.

The new *Salvia* plant is a product of a planned breeding program conducted by the Inventor in Bonsall, Calif. The objective of the breeding program is to create new uniform *Salvia* plants with attractive leaves and flowers and good garden performance.

The new *Salvia* plant originated from a cross-pollination made by the Inventor on Oct. 31, 2016 of a proprietary selection of *Salvia hybrida* identified as code number 16SB119-02, not patented, as the female, or seed, parent with a proprietary selection of *Salvia hybrida* identified as code number 16SB115-03, not patented, as the male, or pollen, parent. The new *Salvia* plant was discovered and selected by the Inventor as a single flowering plant from within the progeny of the stated cross-pollination in a controlled greenhouse environment in Bonsall, Calif. on Aug. 16, 2017.

Asexual reproduction of the new *Salvia* plant by vegetative terminal cuttings in Bonsall, Calif. since Aug. 23, 2017 has shown that the unique features of this new *Salvia* plant are stable and reproduced true to type in successive generations.

SUMMARY OF THE INVENTION

Plants of the new *Salvia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'BBSAL013201'. These characteristics in combination distinguish 'BBSAL013201' as anew and distinct *Salvia* plant:

1. Upright plant habit.
2. Moderately vigorous growth habit and rapid growth rate.
3. Freely branching habit; dense and bushy plant form.
4. Strong and sturdy lateral branches.
5. Dark green-colored leaves.

6. Early and freely flowering habit.
7. Upright inflorescences with purplish blue-colored flowers.
8. Good garden performance.

Plants of the new *Salvia* can be compared to plants of the female parent selection. Plants of the new *Salvia* differ primarily from plants of the female parent selection in the following characteristics:

1. Plants of the new *Salvia* have stronger and sturdier lateral branches than plants of the female parent selection.
2. Leaves of plants of the new *Salvia* are darker green in color than leaves of plants of the female parent selection.
3. Plants of the new *Salvia* and the female parent selection differ in flower color as plants of the new *Salvia* have more bluish-colored flowers whereas plants of the female parent selection have more purplish-colored flowers.
4. Plants of the new *Salvia* have better garden performance than plants of the female parent selection.

Plants of the new *Salvia* can be compared to plants of the male parent selection. Plants of the new *Salvia* differ primarily from plants of the male parent selection in the following characteristics:

1. Plants of the new *Salvia* have stronger and sturdier lateral branches than plants of the male parent selection.
2. Leaves of plants of the new *Salvia* are darker green in color than leaves of plants of the male parent selection.
3. Plants of the new *Salvia* and the male parent selection differ in flower color as plants of the new *Salvia* have purplish blue-colored flowers whereas plants of the male parent selection have pale blue-colored flowers.
4. Plants of the new *Salvia* have better garden performance than plants of the male parent selection.

Plants of the new *Salvia* can be compared to plants of *Salvia hybrida* 'Amistad', disclosed in U.S. Plant Pat. No. 23,578. In side-by-side comparisons, plants of the new *Salvia* differ from plants of 'Amistad' in the following characteristics:

1. Plants of the new *Salvia* are shorter and more upright than plants of 'Amistad'.
2. Plants of the new *Salvia* are more freely branching and denser than plants of 'Amistad'.
3. Plants of the new *Salvia* have stronger and sturdier lateral branches than plants of 'Amistad'.
4. Leaves of plants of the new *Salvia* are broader and darker green in color than leaves of plants of 'Amistad'.

Plants of the new *Salvia* can also be compared to plants of *Salvia guaranitica* 'Black and Blue', not patented. In side-by-side comparisons, plants of the new *Salvia* differ from plants of 'Black and Blue' in the following characteristics:

1. Plants of the new *Salvia* are more freely branching and denser than plants of 'Black and Blue'.
2. Plants of the new *Salvia* have stronger and sturdier lateral branches than plants of 'Black and Blue'.
3. Leaves of plants of the new *Salvia* are broader and darker green in color than leaves of plants of 'Black and Blue'.
4. Plants of the new *Salvia* flower earlier than plants of 'Black and Blue'.
5. Flowers of plants of the new *Salvia* are lighter purplish blue in color than flowers of plants of 'Black and Blue'.

BRIEF DESCRIPTION OF THE PHOTOGRAPHS

The accompanying colored photographs illustrate the overall appearance of the new *Salvia* plant showing the colors as true as it is reasonably possible to obtain in colored reproductions of this type. Colors in the photographs may differ slightly from the color values cited in the detailed botanical description which accurately describe the colors of the new *Salvia* plant.

At the top of the photographic sheet (FIG. 1) is a side perspective view of a typical flowering plant of 'BBSAL01301' grown in a container and at the bottom of the photographic sheet is a close-up view of a typical flowering plant of 'BBSAL01301'.

DETAILED BOTANICAL DESCRIPTION

The aforementioned photographs and following observations and measurements describe plants grown during the spring in 15.25-cm containers in a polyethylene-covered greenhouse in St. Thomas, Ontario, Canada and under cultural practices typical of commercial *Salvia* production. During the production of the plants, day temperatures averaged 27° C. and night temperatures averaged 15° C. Plants were pinched three weeks after planting and were ten weeks from planting rooted cuttings when the photographs and description were taken. In the following description, color references are made to The Royal Horticultural Society Colour Chart, 2007 Edition, except where general terms of ordinary dictionary significance are used.

Botanical classification: *Salvia hybrida* 'BBSAL013201'.

Parentage:

*Female, or seed, parent.*—Proprietary selection of *Salvia hybrida* identified as code number 16SB119-02, not patented.

*Male, or pollen, parent.*—Proprietary selection of *Salvia hybrida* identified as code number 16SB115-03, not patented.

Propagation:

*Type.*—By vegetative terminal cuttings.

*Time to initiate roots, summer.*—About four to five days at temperatures about 17° C. to 29° C.

*Time to initiate roots, winter.*—About seven to nine days at temperatures about 17° C. to 21° C.

*Time to produce a rooted young plant from unrooted cuttings, summer.*—About three to four weeks at temperatures about 17° C. to 29° C.

*Time to produce a rooted young plant from unrooted cuttings, winter.*—About four to five weeks at temperatures about 17° C. to 21° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Herbaceous perennial typically grown as a container and garden plant; upright plant habit; uniform plant and flowering habit; moderately vigorous growth habit and rapid growth rate.

*Branching habit.*—Freely basal branching with about six primary lateral branches each with about two lateral branches developing at every node; bushy and dense appearance.

*Plant height.*—About 64 cm.

*Plant width.*—About 78 cm.

*Lateral branch description.*—Length: About 45.9 cm. Diameter: About 5.4 mm. Internode length: About 6.5 cm. Strength: Strong and sturdy. Aspect: Mostly upright to about 30° to 45° from vertical. Texture and luster: Moderately pubescent, longitudinally ridged; matte. Color, developing: Close to N187A. Color, developed: Close to 147B to 147C tinged with close to N77C.

Leaf description:

*Arrangement.*—Opposite, simple.

*Length.*—About 11.3 cm.

*Width.*—About 6.8 cm.

*Shape.*—Ovate.

*Apex.*—Acuminate.

*Base.*—Rounded to cuneate.

*Margin.*—Crenate to serrate.

*Texture and luster, upper surface.*—Sparsely pubescent and densely pubescent along midrib, slightly rough; slightly glossy.

*Texture and luster, lower surface.*—Sparsely pubescent and moderately pubescent along midrib, slightly rough; matte.

*Venation pattern.*—Pinnate, reticulate.

*Color.*—Developing leaves, upper surface: Close to 138A. Developing leaves, lower surface: Close to 147B. Fully expanded leaves, upper surface: Darker than 147A; venation, close to 145B. Fully expanded leaves, lower surface: More grey than 147B; venation, close to 145D.

*Petioles.*—Length: About 6.5 cm. Diameter: About 2.3 mm. Strength: Moderately strong. Texture and luster, upper and lower surfaces: Smooth, glabrous; matte. Color, upper surface: Close to 144C weakly tinged with close to N77C. Color, lower surface: Close to 146C.

Flower description:

*Flower arrangement and shape.*—Single bilabiate flowers arranged on erect terminal and axillary racemes; freely flowering habit with about 39 to 54 flowers developing per inflorescence and more than 500 flowers developing per plant; flowers face mostly outwardly.

*Fragrance.*—None detected.

*Natural flowering season.*—Early flowering habit, plants begin flowering about six to seven weeks after planting; plants flower from late spring until frost in Southern Ontario, Canada.

*Flower longevity.*—Flowers last about four to five days on the plant; flowers not persistent.

*Flower buds.*—Length: About 1.7 cm. Diameter: About 5 mm. Shape: Clavate. Texture and luster: Densely pubescence, velvety; matte. Color: Close to 93A; at the base, close to 150D.

*Inflorescence height.*—About 23.5 cm.

*Inflorescence diameter.*—About 8.6 cm.

*Flower diameter.*—About 2.1 cm.

*Flower length.*—About 3.8 cm.

*Flower throat diameter.*—About 8 mm.

*Flower tube length.*—About 2.4 cm.

*Flower tube diameter, distally.*—About 8 mm.

*Petals.*—Arrangement: Five petals with two upper petals fused forming a galea and three lower petals fused forming a broader lower protruding lip. Upper galea length: About 1.7 cm. Upper galea width: About 6 mm. Lower lip length: About 1.3 cm. Lower lip width: About 5 mm. Shape: Upper galea, hooded; lower lip, oblong, revolute. Apex: Round. Base: Fused into a narrow tube. Margin: Entire. Texture and luster, upper surface: Scabrous; somewhat glossy. Texture and luster, lower surface: Minute pubescence; somewhat glossy. Texture and luster, throat: Smooth, glabrous; slightly glossy. Texture and luster, tube: Sparsely pubescent; moderately glossy. Color: Galea, when opening and fully opened, upper surface: Close to 96C; venation, close to 96C; color does not fade with development. Galea, when opening and fully opened, lower surface: Close to 97B to 97C; venation, close to 97B to 97C; color does not fade with development. Lower lip, when opening and fully opened, upper surface: Close to 96C to 96D; venation, close to 96C to 96D; color does not fade with development. Lower lip, when opening and fully opened, lower surface: Close to 94D; venation, close to 94D; color does not fade with development. Throat: Close to 97D; venation, close to 96D. Tube: Close to 94A; venation, close to 94A.

*Calyx.*—Arrangement: Five sepals fused to form a tubular bilabiate calyx. Sepal length: About 1.8 cm. Sepal width: About 6 mm. Sepal shape: Roughly deltoid. Sepal apex: Cuspidate. Sepal margin: Entire. Sepal texture and luster, inner surface: Smooth, glabrous; matte. Texture and luster, outer surface: Moderately pubescent; matte. Color: When developing and fully developed, inner surface: Close to 145B. When developing and fully developed, outer surface: Close to N189A; along the veins, close to N186A.

*Peduncles.*—Length: About 8.6 cm. Diameter: About 2.5 mm. Strength: Strong. Aspect: Mostly erect. Texture and luster: Smooth, glabrous; matte. Color: Close to 148A moderately to strongly overlain with close to N77C.

*Pedicels.*—Length: About 7 mm. Diameter: About 1 mm. Strength: Strong, flexible. Aspect: About 45° from peduncle axis. Texture and luster: Moderately to densely pubescent; matte. Color: Close to N187B.

*Reproductive organs.*—Stamens: Quantity per flower: Two. Filament length: About 2 cm. Filament color: Distally, close to 94B and proximally, close to N88A to N88B. Anther size: About 5 mm by 1 mm. Anther shape: Ellipsoidal. Anther color: Close to 93A. Pollen amount: Moderate. Pollen color: Close to 155A. Pistils: Quantity per flower: One. Pistil length: About 4.3 cm. Stigma diameter: Less than 1 mm. Stigma shape: Bipartite. Stigma color: Close to N88A. Style length: About 3.9 cm. Style color: Close to NN155D. Ovary color: Close to 154C.

*Seeds and fruits.*—To date, seed and fruit production has not been observed on plants of the new *Salvia* plant.

Pathogen & pest resistance: To date, plants of the new *Salvia* have not been noted to be resistant to pathogens and pests common to *Salvia* plants.

Garden performance: Plants of the new *Salvia* have exhibited good garden performance and to be tolerant to rain, wind, low temperatures about 2° C. and to be suitable for USDA Hardiness Zone 10a to 11b.

It is claimed:

1. A new and distinct *Salvia* plant named 'BBSAL013201' as illustrated and described.

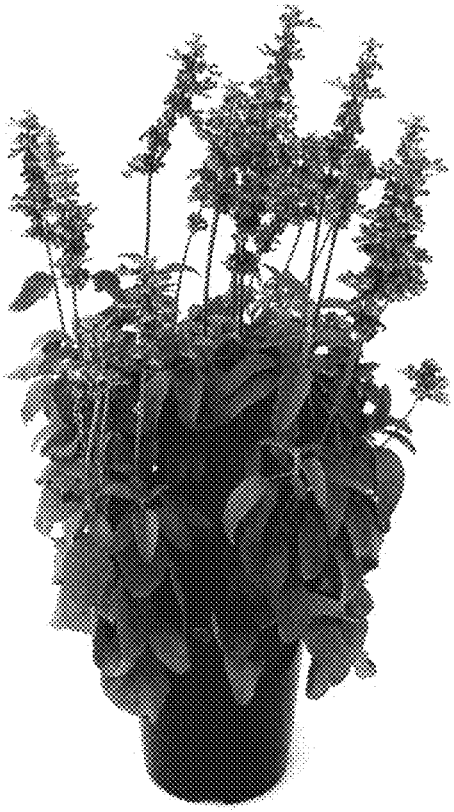
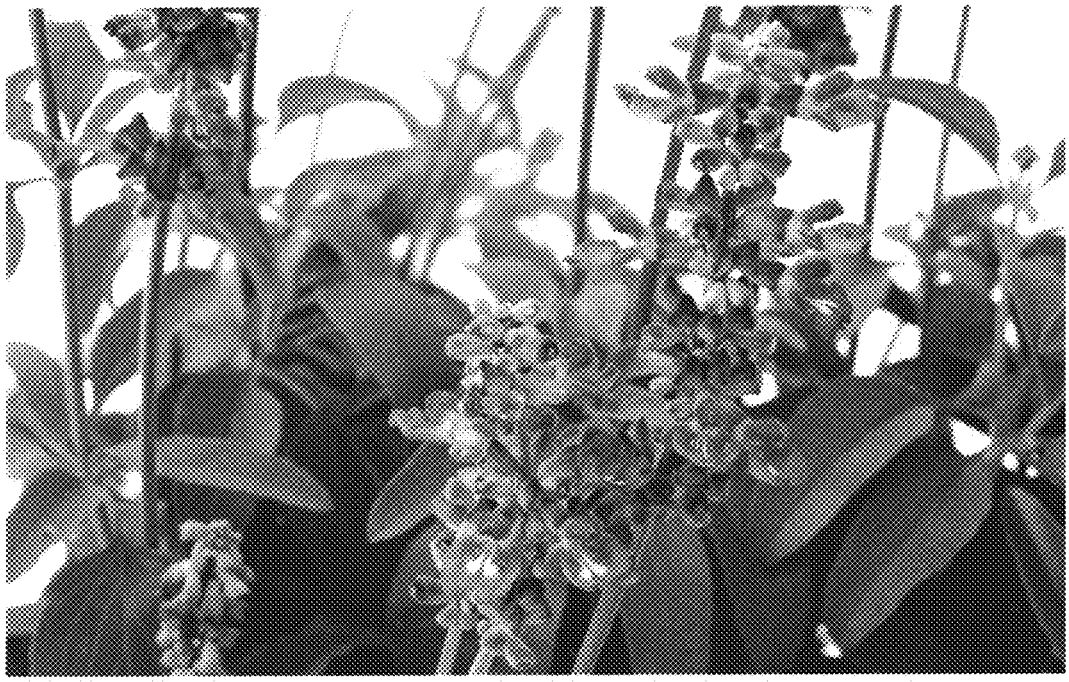

* * * * *